United States Patent [19]

Flagg

[11] 4,440,943

[45] Apr. 3, 1984

[54] PHENOXIODININ-5-IUM ANTIMICROBIAL COMPOUNDS

[75] Inventor: Edward E. Flagg, Midland, Mich.

[73] Assignee: The Dow Chemical Company, Midland, Mich.

[21] Appl. No.: 358,148

[22] Filed: Mar. 15, 1982

[51] Int. Cl.$^3$ ............................................. C07C 63/14
[52] U.S. Cl. ........................................ 560/65; 544/87; 544/121; 544/130; 544/330; 544/357; 544/360; 544/383; 546/188; 546/216; 546/229; 560/12; 560/14; 560/52; 560/53; 562/429; 562/430; 562/460; 562/463; 562/474; 564/83; 564/85; 564/89; 568/326; 568/331; 568/639
[58] Field of Search ................ 560/65, 14, 53, 52, 560/12; 562/474, 463, 460, 429, 430; 568/326, 331, 38; 564/83, 85, 89

[56] References Cited

U.S. PATENT DOCUMENTS

| | | | |
|---|---|---|---|
| 3,244,636 | 4/1966 | Reiler et al. | 252/107 |
| 3,506,719 | 4/1970 | Cannon | 260/612 |
| 4,193,935 | 3/1980 | Cannon | 260/505 R |
| 4,283,349 | 8/1981 | Cannon | 260/505 R |

FOREIGN PATENT DOCUMENTS 115722  4/1970  Denmark .

OTHER PUBLICATIONS

Beringen et al., J. Org. Chem., vol. 30 (1965), pp. 1141-1148.
Eli Lilly & Co., Chemical Abstracts, vol. 64 (1966), 8210h.
Cannon, Chemical Abstracts, vol. 66 (1967), 85799c.
Lilly, Eli & Co., Chemical Abstracts, vol. 77, (1972), 5531y.

Primary Examiner—Richard Raymond
Attorney, Agent, or Firm—Edward P. Gray; Ronald G. Brookens

[57] ABSTRACT

3,7-Substituted phenoxiodinin-5-ium compounds are effective against a variety of aerobic and anaerobic bacteria as well as fungi. The compounds of this invention may be prepared by the direct iodination of a suitably substituted diphenyl ether with iodosyl sulfate in concentrated sulfuric acid. The resulting bisulfate anion may be exchanged with a desired anion by standard metathetic processes.

22 Claims, No Drawings

PHENOXIODININ-5-IUM ANTIMICROBIAL COMPOUNDS

BACKGROUND OF THE INVENTION

This invention relates to a group of biologically active iodonium compounds which exhibit antimicrobial effects against a variety of bacteria and fungi.

SUMMARY OF THE INVENTION

The present invention is directed to compounds of the formula:

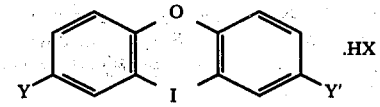  (I)

wherein X is an anion, and Y and Y' each independently represent:
(a) alkyl;
(b) carboxyl (

provided that when both Y and Y' are carboxyl, X is bromo);
(c) alkylcarbonyl (

wherein R represents alkyl);
(d) alkyloxycarbonyl (

wherein R represents alkyl);
(e) substituted alkylcarbonyl of the formula

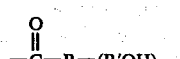

wherein R and R' are each independently alkyl, and m is an integer of from one to six, both inclusive;
(f) adamantanoyl, i.e.,

(g) substituted carbonyl of the formula

wherein T represents:
(1) N-alkyl-substituted pyrazine,
(2) N,N-dialkyl-substituted pyrazine, or
(3) phenylalkylether;
(h) sulfonyl radicals of the formula

—SO$_2$—Q wherein Q represents:
(1) halo,
(2) mono or dialkyl-substituted amino, or
(3) —N, wherein Z represents the atoms completing a morpholino, piperidino, piperazino, or N-alkyl-piperazino group.

As used herein, the term "alkyl" refers to aliphatic straight or branched chain radicals of from about one to about six carbon atoms, both inclusive; the term "halo" refers to atoms selected from the group consisting of chlorine, bromine, or fluorine; the term "anion" refers to inorganic anions such as chloride, bromide, iodide, sulfate, nitrate, phosphate or phosphonate, and organic anions such as acetate, propionate, maleate, citrate, or tartrate.

Preferred compounds of the present invention, are those compounds wherein X is an anion selected from the group consisting of bromide, chloride and sulfate, and Y and Y' are each independently —SO$_2$—Q. Of these preferred compounds, those compounds wherein Q is mono or dialkyl-substituted amino are especially preferred.

Other preferred compounds of the present invention are those compounds wherein X is an anion selected from the group consisting of bromide, chloride and sulfate, and Y and Y' are each independently alkylcarbonyl. Of these preferred compounds, those compounds wherein the alkyl moiety is methyl or ethyl are especially preferred.

The compounds of the present invention are biologically active and useful as antimicrobial agents against a variety of aerobic and anaerobic bacteria and fungi. These compounds are typically effective against organisms such as *Staphylococcus aureus, Salmonella typhosa, Bacillus subtilis, Candida pelliculosa, Proteus mirabilis, Streptococcus mutans, Escherichia coli,* and *Trichophyton mentagrophytes.*

The broad class of compounds referred to herein as phenoxiodinin-5-ium compounds are also variously referred to in the literature as dibenz[be][1,4]oxiodinium compounds or pheniodoxin-5-ium compounds.

The specific phenoxiodinin-5-ium compounds of the present invention can be prepared by various methods. (See for example, V. Migrdichian, *Organic Synthesis,* Reinhold Publishers, 1957.) One such process involves the direct iodination of a suitably substituted diphenyl ether with iodosyl sulfate (IO)$_2$SO$_4$ in concentrated sulfuric acid. The resulting bisulfate anion may then be exchanged with the desired acid anion by standard metathetic processes.

Other methods for preparing phenoxiodinin-5-ium compounds are known in the art (see U.S. Pat. No. 3,244,636). One method involves the tetra-azotizing of an appropriate 2,2'-diaminodiphenyloxide. The iodonium compound may be obtained by allowing the tetra-azotate to decompose in the presence of an aqueous solution of potassium iodide or other iodide salt. Another method involves the oxidation of o-iodobiphenyl or o-iodobiphenyl alkane by peracetic acid. The corresponding iodoso acetate is reduced with sulfuric acid to the heterocyclic phenoxiodinin-5-ium compound. Still another method involves the chlorination of o-iodobiphenyl or o-iodobiphenyl alkane to the iododichloride compound. The iododichloride compound may then be reacted with alkali forming the corresponding iodoso compound. Treatment with sulfuric acid or other strong Lewis acids yields the heterocyclic phenoxiodinin-5-ium compound.

DESCRIPTION OF SOME PREFERRED EMBODIMENTS

The following examples are merely illustrative, and are not intended as a limitation on the invention.

EXAMPLE 1

3,7-Diacetylphenoxiodinin-5-ium chloride dihydrate

4-Acetylphenylether,

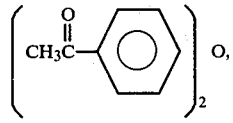

was prepared from acetyl chloride, diphenyl ether and aluminum chloride by a process known in the art. (See, for example, Tomita, *J. Pharm. Soc. Japan,* 57, 689 (1937).)

Iodine (2.4 grams), potassium iodate (7.9 grams) and 100 milliliters (ml) of concentrated sulfuric acid (96.6%) were stirred overnight at ambient temperature (satisfactory yields may be obtained within about three hours). The resulting mixture contained the desired iodosyl sulfate, $(IO)_2SO_4$.

After cooling to about $-22°$ C., the 4-acetylphenylether (12.5 grams) was slowly added (with stirring) to the iodosyl sulfate solution. This mixture was cooled to around $-40°$ C. and then allowed to warm to ambient temperature overnight. Isolation of a solid was achieved by pouring the iodosyl sulfate mixture over about 800 grams of ice, cooling the mixture in a refrigerator, filtering and drying over nitrogen. The solid, 3,7-diacetylphenoxiodinin-5-ium bisulfite hemihydrate, was recrystallized from a mixture of formic acid and acetone. The chloride salt was prepared by treating the formic acid solution with 37% hydrochloric acid. Recrystallization of the chloride salt was achieved from a mixture of formic acid and alcohol. The compound, 3,7-diacetylphenoxiodinin-5-ium chloride dihydrate melted at 268°–270° C.

Analysis: Calculated (percent): Carbon—42.6; Hydrogen—3.58. Found (percent): Carbon—42.4; Hydrogen—2.78.

By utilizing the process outlined above, the bromide salt was prepared by treating the formic acid solution of the bisulfate salt with 48% hydrobromic acid and recrystallizing from a mixture of formic acid and alcohol. The resulting compound, 3,7-diacetylphenoxiodinin-5-ium bromide monohydrate melted at 259°–261° C.

Analysis: Calculated (percent): Carbon—40.3; Hydrogen—2.96. Found (percent): Carbon—40.3; Hydrogen—2.74.

EXAMPLE 2

3,7-Dipropionylphenoxiodinin-5-ium chloride hemihydrate

Diphenyl ether (67 grams) was mixed with about 79 grams of propionyl chloride and 109 grams of aluminum chloride in about 150 ml of carbon disulfide. The product, 4-propionylphenyl ether, was isolated by hydrolysis of the mixture and conventional recrystallization techniques.

Iodine (2.52 grams), potassium iodate (8.49 grams), and about 65 ml of concentrated sulfuric acid were stirred together at ambient temperature for about 26 hours. Solid 4-propionylphenyl ether (14 grams) was added slowly to the above solution using about 20 ml of concentrated sulfuric acid as a rinse solution. The stirred mixture was initially cooled to about 5° C. but was allowed to warm to ambient temperature overnight. This solution was then poured over about 800 grams of ice and filtered, leaving the insoluble bisulfate salt which was then recrystallized from a mixture of formic acid and acetone. The chloride salt was prepared by treating the warm formic acid-acetone mixture with 37% hydrochloric acid. The purified compound, 3,7-dipropionylphenoxiodinin-5-ium chloride hemihydrate melted at 242°–244° C.

Analysis: Calculated (percent): Carbon—47.8; Hydrogen—3.82. Found (percent): Carbon—47.6; Hydrogen—3.83.

EXAMPLE 3

3-Carboxy-7-(methoxycarbonyl)phenoxiodinin-5-ium chloride monohydrate

Iodine (2.6 grams), potassium iodate (9.6 grams), and concentrated sulfuric acid (100 ml) were stirred together overnight at ambient temperature. Slowly added to this solution was 14 grams of dimethyl-4,4'-oxydibenzoate, prepared by the reaction of 4,4'-dibromophenylether and carbon monoxide, with nickel carbonyl as a catalyst. After stirring overnight, the mixture was poured over ice and filtered leaving the bisulfate salt as a precipitate which was redissolved in methanol, treated with activated carbon and again filtered. The filtrate was dried over nitrogen and warmed in a vacuum oven at about 45° C. The bisulfate salt was again dissolved in methanol and treated with an aqueous solution of sodium chloride leaving the desired, 3-carboxy-7-(methoxycarbonyl)-phenoxiodinin-5-ium chloride monohydrate with a melting point of 245°–246° C.

Analysis: Calculated (percent): Carbon—40.0; Hydrogen—2.68. Found (percent): Carbon—39.8; Hydrogen—2.62.

Following a procedure substantially the same as that described above, the bromide salt was prepared by treating the methanol solution of the bisulfate salt with an aqueous solution of sodium bromide. The compound which was obtained, 3-carboxy-7-(methoxycarbonyl)-phenoxiodinin-5-ium bromide monohydrate, melted at 235°–236° C.

Analysis: Calculated (percent): Carbon—36.4; Hydrogen—2.44. Found (percent): Carbon—36.2; Hydrogen—2.30.

EXAMPLE 4

3,7-bis((4-Methyl-1-piperazinyl)sulfonyl)phenoxiodinin-5-ium bromide, hydrobromide Oxybis-(4,1-phenylene sulfonyl)bis-(4-methyl piperazine),

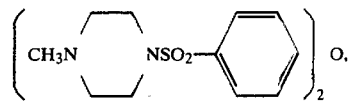

was prepared by treating the corresponding chloride,

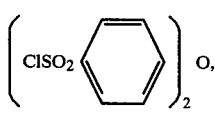

with excess methyl piperazine in methanol.

Iodine (0.7 gram), potassium iodate (2.2 grams) and concentrated sulfuric acid (50 ml) were stirred overnight at ambient temperature. 5.9 Grams of oxybis(4,1-phenylene sulfonyl)bis-(4-methyl piperazine) was added at 0° C. The temperature was maintained at less than 5° C. for several hours before the solution was poured over about 600 grams of ice. Cooling overnight in a refrigerator yielded a small amount of precipitate which was separated by filtration. The filtrate was treated with sodium bromide (or alternatively, 48% hydrobromic acid) and dried by conventional techniques leaving the solid 3,7-bis((4-methyl-1-piperazinyl)sulfonyl)phenoxiodinin-5-ium hydrobromide which contained about 2.5 HBr (coordinated) per organic cation. The compound melted with decomposition at 230° C.

Analysis: Calculated (percent): Carbon—29.3; Hydrogen—3.41; Nitrogen—6.21. Found (percent): Carbon—28.6; Hydrogen—3.46; Nitrogen—6.26.

Following substantially the same procedure as outlined in Example 4, the following compounds were prepared:

EXAMPLE 5
3,7-Bis(4-morpholinylsulfonyl)phenoxiodinin-5-ium sulfate hydrate, melting at 200°–203° C.

EXAMPLE 6
3,7-Bis(dimethylaminosulfonyl)phenoxiodinin-5-ium bromide, melting at 272°–273° C.

EXAMPLE 7
3,7-Bis(dimethylaminosulfonyl)phenoxidinin-5-ium chloride, melting at 286°–287° C.

EXAMPLE 8
3,7-Bis(methylaminosulfonyl)phenoxiodinin-5-ium bromide hemihydrate, melting at 237°–239° C.

EXAMPLE 9
3,7-Bis(methylaminosulfonyl)phenoxiodinin-5-ium chloride, melting at 245°–246.5° C.

EXAMPLE 10
3,7-Bis(methylaminosulfonyl)phenoxiodinin-5-ium sulfate, melting at 198°–201° C.

Utilizing substantially the same procedures as described in the above examples, various other phenoxiodinin-5-ium compounds and their salts have been prepared. The physical properties of those compounds as well as those described in the preceding examples are set out in Table I, wherein the compound number in Table I (Compound No.) does not necessarily correspond with the example number previously designated for a given compound.

TABLE I

| Compound No. | Y | Y' | X | Melting Point (°C.) | Found %C | Found %H | Found %N | Calculated %C | Calculated %H | Calculated %N |
|---|---|---|---|---|---|---|---|---|---|---|
| 1 | −C(=O)−CH₂ | −C(=O)−CH₃ | (a) Cl(2H₂O) | 268–270 | 42.4 | 2.78 | | 42.6 | 3.58 | |
| | | | (b) Br(H₂O) | 259–261 | 40.3 | 2.74 | | 40.3 | 2.96 | |
| | | | (c) SO₄(0.5 H₂O) | 245–248 | 39.6 | 2.89 | | 39.6 | 2.91 | |
| 2 | −C(=O)−C₂H₅ | −C(=O)−C₂H₅ | (a) Cl(0.6 H₂O) | 242–244 | 47.6 | 3.83 | | 47.8 | 3.82 | |
| | | | (b) SO₄ | 171–173 | 42.7 | 2.99 | | 42.9 | 3.40 | |
| 3 | −C(=O)−OH | −C(=O)−O−CH₃ | (a) Cl(H₂O) | 245–246 | 39.8 | 2.62 | | 40.0 | 2.68 | |
| | | | (b) Br(H₂O) | 235–236 | 36.2 | 2.30 | | 36.4 | 2.44 | |
| | | | (c) SO₄(H₂O) | 233–236 | 35.6 | 2.56 | | 35.2 | 2.56 | |
| 4 | −S(=O)₂−N(piperazinyl-NCH₃) | −S(=O)₂−N(piperazinyl-NCH₃) | (a) Br(2.5 HBr) | 230-decomp | 28.6 | 3.46 | 6.26 | 29.3 | 3.41 | 6.21 |
| 5 | C=O (camphor-like) | C=O (camphor-like) | (a) Cl | 250–252 | 58.7 | 5.17 | | 58.9 | 5.80 | |
| | | | (b) Br | 236–238 | 54.1 | 4.82 | | 54.2 | 5.62 | |
| | | | (c) SO₄ | 96–99 | 57.3 | 5.20 | | 57.0 | 5.20 | |
| 6 | −C(=O)−OH | −C(=O)−OH | (a) Br(2H₂O) | 240–241 | 33.9 | 2.10 | | 33.7 | 2.42 | |

TABLE I-continued

[Structure: Y-phenyl-O-phenyl-Y' · HX]

| Compound No. | Y | Y' | X | Melting Point (°C.) | Found %C | Found %H | Found %N | Calculated %C | Calculated %H | Calculated %N |
|---|---|---|---|---|---|---|---|---|---|---|
| 7 | -S(O)₂-N(CH₃)H | -S(O)₂-N(CH₃)H | (a) Br(0.5 H₂O) | 237-239 | 27.5 | 2.53 | 4.82 | 30.0 | 2.52 | 4.99 |
|   |   |   | (b) Cl | 245-246.5 | 32.4 | 2.80 | 5.54 | 32.5 | 2.73 | 5.42 |
|   |   |   | (c) SO₄ | 198-201 | 29.3 | 2.65 | 4.98 | 29.1 | 2.61 | 4.84 |
| 8 | -S(O)₂-morpholino | -S(O)₂-morpholino | (a) SO₄(H₂O) | 200-203 | 35.9 | 3.46 | 4.62 | 36.4 | 3.74 | 4.25 |
| 9 | -S(O)₂-N(CH₃)₂ | -S(O)₂-N(CH₃)₂ | (a) Br | 272-273 | 32.6 | 3.15 | 4.79 | 32.6 | 3.08 | 4.75 |
|   |   |   | (b) Cl | 286-287 | 35.1 | 3.36 | 5.31 | 35.3 | 3.33 | 5.14 |
|   |   |   | (c) SO₄(H₂O) |  | 33.2 | 3.29 | 4.81 | 33.7 | 3.67 | 4.86 |

The compounds of the present invention are useful as antibacterial agents, antifungal agents, or both. Their effectiveness varies with the concentration of compound employed and the particular organisms tested. While not all compounds are effective at similar concentrations against the same organisms, all compounds of the present invention may be utilized as antibacterial agents, antifungal agents or both.

Examples of the bacteria and fungi controlled by effective amounts of one or more of the compounds are *Staphylococcus aureus, Salmonella typhosa, Escherichia coli, Proteus mirabilis, Bacillus subtilis, Streptococcus mutans, Enterobacter aerogenes, Ceratocystis ips,* and *Trichophyton mentagrophytes.* The activity of certain compounds of the present invention against the known cariogenic organism, *Streptococcus mutans,* also makes them useful in the treatment of dental pathologies such as caries and periodontal disease. As used herein, the term "effective amount" refers to that amount of one or more of the compounds needed to exhibit either static or cidal effects on selected organisms. Typically, this amount varies from about 0.5 to about 500 parts per million (ppm) by weight depending upon the particular compound tested and organism treated.

The antimicrobial activity of the compounds of this invention was demonstrated by the following techniques:

A tube containing 30 ml of trypticase soy agar was melted and warmed to 45° C. The test compound was added to the tube at a concentration of 0.05% (500 ppm). The mixture was stirred and poured into plates to harden. When hardened, the plates were inoculated with various aerobic and anaerobic organisms. The aerobic plates were incubated at 37° C. for 24 hours and then read for bacterial growth. The same plates were again incubated at 30° C. for an additional 48 hours at which point they were checked for yeast and fungal growth. The anaerobic plates were incubated at 37° C. in an anaerobic chamber and read at 48 hours.

After the initial readings, compounds showing sufficient activity were re-tested at various concentrations to determine the minimum inhibitory concentration (MIC) of the compounds of the invention against various bacteria and fungi. The results of these tests are summarized in Table II.

TABLE II

| Compound | MINIMUM INHIBITORY CONCENTRATIONS (PPM) Test Organisms** | | | | | | | | | |
|---|---|---|---|---|---|---|---|---|---|---|
| No.* | Sa | St | Ec | Pm | Bs | Sm | An | Af | Tm | Cp |
| 1(a) | 5 | 10 | 50 | 100 | 5 | NI[1] | NI[1] | 500 | 500 | NI[1] |
| 1(b) | 5 | 10 | 50 | 500 | 5 | NI[1] | NI[1] | 500 | 100 | NI[1] |
| 1(c) | 5 | 5 | 10 | 50 | 1.0 | NI[1] | NI[1] | 500 | 100 | NI[1] |
| 2(a) | 10 | 50 | 50 | 100 | 50 | NI[1] | NI[1] | NI[1] | 500 | NI[1] |
| 2(b) | 500 | NI[1] | NI[1] | NI[1] | 500 | NI[1] | NR[2] | NR[2] | NR[2] | NI[1] |
| 3(a) | 5 | 10 | 10 | 10 | 1.0 | 500 | 500 | 50 | 500 | 500 |
| 3(b) | 1.0 | 5 | 5 | 5 | 0.5 | 10 | 500 | 100 | 100 | 500 |
| 3(c) | 1.0 | 5 | 5 | 5 | 0.5 | 500 | 500 | 100 | 100 | 500 |
| 4(a) | 50 | 500 | 500 | NI[1] | 100 | NI[1] | NR[2] | NR[2] | NR[2] | NI[1] |
| 5(a) | 12.5 | NR[2] | NI[1] | NI[1] | NR[2] | 3.12 | NI[1] | NR[2] | NR[2] | NR[2] |
| 5(b) | 0.78 | NR[2] | NI[1] | NI[1] | NR[2] | 0.78 | NI[1] | NR[2] | NR[2] | **Sa |
| 6(a) | 1.0 | 10 | 5 | 50 | 0.5 | 500 | NR[2] | NR[2] | NR[2] | NR[2] |
| 7(a) | 500 | NI[1] | NR[2] | NR[2] | NR[2] | NI[1] | NI[1] | NR[2] | NR[2] | NR[2] |
| 7(b) | 500 | 500 | 500 | NR[2] | NR[2] | 500 | 500 | NR[2] | NR[2] | NR[2] |
| 9(a) | 500 | NI[1] | NI[1] | NI[1] | 500 | NI[1] | NI[1] | NI[1] | NI[1] | NI[1] |

TABLE II-continued

| Compound | MINIMUM INHIBITORY CONCENTRATIONS (PPM) Test Organisms** | | | | | | | | |
|---|---|---|---|---|---|---|---|---|---|
| No.* | Sa | St | Ec | Pm | Bs | Sm | An | Af | Tm | Cp |
| 9(b) | 500 | NI$^{(1)}$ | NI$^{(1)}$ | NI$^{(1)}$ | 500 | NI$^{(1)}$ | NI$^{(1)}$ | NI$^{(1)}$ | NI$^{(1)}$ | NI$^{(1)}$ |

*From TABLE I
** Sa = *Staphylococcus aureus*
St = *Salmonella typhosa*
Ec = *Escherichia coli*
Pm = *Proteus mirabilis*
Bs = *Bacillus subtilis*
**An = *Aspergillus niger*
Af = *Aspergillus fumigatus*
Tm = *Trichophyton mentagrophytes*
Cp = *Candida pelliculosa*
Sm = *Streptococcus mutans*
$^{(1)}$NI = No Inhibition
$^{(2)}$NR = Not Run (ie., not tested against the organisms specified)

In another procedure, the minimum inhibitory concentration (MIC) and minimum bactericidal concentration (MBC) were determined in ppm for various compounds of the invention against the bacteria, *Streptococcus mutans* (ATCC 10449). The testing was performed using Todd Hewitt broth and standard dilution techniques. The data obtained are compiled in Table III.

In still another operation, the acid inhibiting property of these compounds was tested against the known acid producing organism, *Streptococcus mutans*. Test tubes containing Trypticase-yeast medium with sucrose were inoculated with *S. mutans* and incubated for 48 hours at 37° C. The tubes were then titrated with 0.1 N sodium hydroxide. The minimum concentration of compound (in ppm) which prevented acid formation was recorded and is summarized in Table III.

TABLE III

| Compound | Organism: Streptococcus mutans | | |
|---|---|---|---|
| No.* | MIC (ppm) | MBC (ppm) | Acid Inhibition (ppm) |
| 1(a) | 0.49 | 0.98 | 0.12 |
| 1(b) | 0.1 | 0.5 | 0.1 |
| 1(c) | 1.0 | 8.0 | 0.5 |
| 2(a) | 2.0 | 0.5 | 0.1 |
| 2(b) | 125 | 31 | 7.8 |
| 3(a) | 2.0 | 2.0 | 1.0 |
| 3(b) | 2.0 | 1.0 | 1.0 |
| 3(c) | 1.0 | 2.0 | 1.0 |
| 4(a) | ≧63 | ≧63 | — |
| 5(a) | 3.12 | 3.12 | — |
| 5(b) | 0.78 | 1.56 | — |
| 6(a) | 3.9 | 3.9 | 3.9 |
| 8(a) | 62.5 | >125 | 8.0 |
| 9(a) | >125 | >125 | 0.2 |
| 9(b) | >125 | >125 | 0.03 |

*From TABLE I

What is claimed is:

1. A compound corresponding to the formula:

$$\text{Y} \underset{\text{I}}{\overset{}{\bigcirc}} - \text{O} - \bigcirc - \text{Y}' \cdot \text{HX}$$

wherein X is an anion, and Y and Y' each independently represent:

(a)

$$-\overset{\text{O}}{\underset{\|}{\text{C}}}-\text{OH},$$

provided that when both Y and Y' are carboxyl, X is bromo;

(b)

$$-\overset{\text{O}}{\underset{\|}{\text{C}}}-\text{R},$$

wherein R represents alkyl;

(c)

$$-\overset{\text{O}}{\underset{\|}{\text{C}}}-\text{OR},$$

wherein R represents alkyl;

(d)

$$-\overset{\text{O}}{\underset{\|}{\text{C}}}-\text{R}-(\text{R'OH})_m,$$

wherein R and R' are each independently alkyl, and m is an integer of from one to six, both inclusive;

(e) adamantanoyl, i.e., $$-\overset{\text{O}}{\underset{\|}{\text{C}}}-\text{adamantyl};$$

(f)

$$-\overset{\text{O}}{\underset{\|}{\text{C}}}-\text{T},$$

wherein T represents:
phenylalkylether;

(g)
     $-SO_2-Q$ wherein Q represents:
(1) halo or
(2) mono or dialkyl-substituted amino.

2. The compound of claim 1 wherein Y and Y' are each independently $-SO_2-Q$, and X is an anion selected from the group consisting of bromide, chloride and sulfate.

3. The compound of claim 1 wherein Y and Y' are each independently alkylcarbonyl, and X is an anion selected from the group consisting of chloride, bromide and sulfate.

4. The compound of claim 1 which is 3-carboxy-7-(methoxycarbonyl)-phenoxiodinin-5-ium chloride monohydrate.

5. The compound of claim 1 which is 3-carboxy-7-(methoxycarbonyl)-phenoxiodinin-5-ium bromide monohydrate.

6. The compound of claim 1 which is 3-carboxy-7-(methoxycarbonyl)phenoxiodinin-5-ium sulfate monohydrate.

7. The compound of claim 1 which is 3,7-diadamantanoylphenoxiodinin-5-ium chloride.

8. The compound of claim 1 which is 3,7-diadamantanoylphenoxiodinin-5-ium bromide.

9. The compound of claim 1 which is 3,7-dicarboxylphenoxiodinin-5-ium bromide dihydrate.

10. The compound of claim 2 wherein Q is monoalkylsubstituted amino.

11. The compound of claim 2 wherein Q is dialkylsubstituted amino.

12. The compound of claim 3 wherein the alkyl moiety is methyl.

13. The compound of claim 3 wherein the alkyl moiety is ethyl.

14. The compound of claim 10 which is 3,7-bis(methylaminosulfonyl)phenoxiodinin-5-ium bromide hemihydrate.

15. The compound of claim 10 which is 3,7-bis(methylaminosulfonyl)phenoxiodinin-5-ium chloride.

16. The compound of claim 11 which is 3,7-bis(dimethylaminosulfonyl)phenoxiodinin-5-ium bromide.

17. The compound of claim 11 which is 3,7-bis(dimethylaminosulfonyl)phenoxiodinin-5-ium chloride.

18. The compound of claim 12 which is 3,7-diacetylphenoxiodinin-5-ium chloride dihydrate.

19. The compound of claim 12 which is 3,7-diacetylphenoxiodinin-5-ium bromide hydrate.

20. The compound of claim 12 which is 3,7-diacetylphenoxiodinin-5-ium sulfate hemihydrate.

21. The compound of claim 13 which is 3,7-dipropionylphenoxiodinin-5-ium chloride hemihydrate.

22. The compound of claim 13 which is 3,7-dipropionylphenoxiodinin-5-ium sulfate.

* * * * *

UNITED STATES PATENT AND TRADEMARK OFFICE
CERTIFICATE OF CORRECTION

PATENT NO. : 4,440,943
DATED : April 3, 1984
INVENTOR(S) : Edward E. Flagg

It is certified that error appears in the above—identified patent and that said Letters Patent is hereby corrected as shown below:

Col. 2, line 52, "(IO)$_2$SO$_4$)" should read -- ((IO)$_2$SO$_4$) --.

Col. 3, line 41, "bisulfite" should read -- bisulfate --.

Cols. 5-6, Table I, 1st compound, col. 2 under "Y" should read

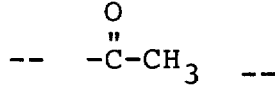

Cols. 7-8, Table II, Compound No. 5(b), last col. under "Cp" "**Sa" should read -- NR$^{(2)}$ --

Signed and Sealed this

*Twenty-fifth* Day of *September 1984*

[SEAL]

Attest:

GERALD J. MOSSINGHOFF

*Attesting Officer*  *Commissioner of Patents and Trademarks*